(12) United States Patent
Daxer

(10) Patent No.: US 10,064,753 B2
(45) Date of Patent: Sep. 4, 2018

(54) DEVICE AND METHOD FOR IRRADIATING THE EYE

(71) Applicant: Albert Daxer, Wilhering (AT)

(72) Inventor: Albert Daxer, Wilhering (AT)

( * ) Notice: Subject to any disclaimer, the term of this patent is extended or adjusted under 35 U.S.C. 154(b) by 0 days.

(21) Appl. No.: 15/680,421

(22) Filed: Aug. 18, 2017

(65) Prior Publication Data

US 2017/0340481 A1    Nov. 30, 2017

Related U.S. Application Data

(62) Division of application No. 14/436,198, filed as application No. PCT/EP2013/070345 on Sep. 30, 2013.

(30) Foreign Application Priority Data

Oct. 17, 2012  (AT) .................................. 1122/2012

(51) Int. Cl.
*A61B 18/18*    (2006.01)
*A61F 9/007*    (2006.01)
(Continued)

(52) U.S. Cl.
CPC .......... *A61F 9/0079* (2013.01); *A61B 3/0008* (2013.01); *A61F 9/008* (2013.01); *A61F 9/009* (2013.01); *A61F 2009/00893* (2013.01)

(58) Field of Classification Search
CPC .......... A61F 9/008; A61B 18/20; A61B 18/22
(Continued)

(56) References Cited

U.S. PATENT DOCUMENTS 6,161,544 A * 12/2000 DeVore ................... A61F 9/008
                                                128/898
2003/0111327 A1* 6/2003 Metzler .................... H01H 3/14
                                                200/86.5
(Continued)

FOREIGN PATENT DOCUMENTS

EP    1 561 440 A1    8/2005
EP    2 327 383 A1    6/2011
(Continued)

OTHER PUBLICATIONS

International Search Report of PCT/EP2013/070345, dated Jan. 7, 2014.
(Continued)

*Primary Examiner* — Daniel Cerioni
(74) *Attorney, Agent, or Firm* — Collard & Roe, P.C.

(57) ABSTRACT

A device and a method for irradiating the cornea of an eye, wherein the device includes at least the following elements: a ring body, which has a bearing surface embodied concentrically about the longitudinal axis of the device for the purpose of fastening the device on the eye, an irradiation channel for irradiating the cornea, which is located inside the ring body, a light source, which, in the operationally-ready state of the device, is attached inside the ring body for emitting light in the irradiation channel, wherein the bearing surface for fastening the device is arranged outside the irradiation channel, which has the result that the irradiated area itself is not additionally loaded by bearing surfaces of the device.

13 Claims, 6 Drawing Sheets

(51) Int. Cl.
    *A61F 9/009*     (2006.01)
    *A61B 3/00*     (2006.01)
    *A61F 9/008*     (2006.01)

(58) Field of Classification Search
    USPC .......................................................... 606/3
    See application file for complete search history.

(56) References Cited

U.S. PATENT DOCUMENTS

| | | | |
|---|---|---|---|
| 2008/0140164 A1* | 6/2008 | Oberreiter | A61N 5/0616 |
| | | | 607/88 |
| 2008/0208177 A1 | 8/2008 | Mrochen et al. | |
| 2009/0209954 A1 | 8/2009 | Muller et al. | |
| 2011/0034973 A1* | 2/2011 | Wang | A61B 18/22 |
| | | | 607/89 |
| 2011/0190741 A1 | 8/2011 | Deisinger et al. | |
| 2011/0190742 A1 | 8/2011 | Anisimov | |
| 2011/0205492 A1 | 8/2011 | Rathjen | |
| 2011/0313344 A1* | 12/2011 | Daxer | A61F 9/013 |
| | | | 604/22 |
| 2012/0157977 A1* | 6/2012 | Hulliger | A61B 17/8863 |
| | | | 606/13 |
| 2012/0310141 A1* | 12/2012 | Kornfield | A61F 9/008 |
| | | | 604/20 |
| 2013/0116757 A1 | 5/2013 | Russmann | |
| 2014/0048134 A1* | 2/2014 | Liang | H01L 31/0547 |
| | | | 136/259 |
| 2014/0114232 A1* | 4/2014 | Hafezi | A61F 9/0079 |
| | | | 604/20 |

FOREIGN PATENT DOCUMENTS

| | | |
|---|---|---|
| WO | 2010/022745 A1 | 3/2010 |
| WO | 2011/138031 A1 | 11/2011 |
| WO | 2012/047307 A1 | 4/2012 |
| WO | 2012/127330 A1 | 9/2012 |
| WO | 2013/059837 A2 | 4/2013 |

OTHER PUBLICATIONS

A. Daxer et al., "Corneal Crosslinking and Visual Rehabilitation in Keratoconus in One Session Without Epithelial Debridement: New Technique," Cornea, Oct. 2010, vol. 29, No. 10, pp. 1176-1179.

* cited by examiner

DEVICE AND METHOD FOR IRRADIATING THE EYE

CROSS REFERENCE TO RELATED APPLICATIONS

This application is a divisional of and Applicant claims priority under 35 U.S.C. §§ 120 and 121 of U.S. application Ser. No. 14/436,198 filed on Apr. 16, 2015, which application is a national stage application under 35 U.S.C. § 371 of PCT Application No. PCT/EP2013/070345 filed on Sep. 30, 2013, which claims priority under 35 U.S.C. § 119 from Austrian Patent Application No. A 1122/2012 filed on Oct. 17, 2012, the disclosures of each of which are hereby incorporated by reference. A certified copy of priority Austrian Patent Application No. A 1122/2012 is contained in parent U.S. application Ser. No. 14/436,198. The International Application under PCT article 21(2) was not published in English.

BACKGROUND OF THE INVENTION

1. Field of the Invention

The invention relates to a device and a method for irradiating the—preferably human—eye, in particular the cornea. The device according to the invention and the method according to the invention are directed to inducing changes in the structure of the corneal stroma, which counteract pathological changes. Thus, for example, keratoconus is a disease of the cornea, which results in increasing weakening of the mechanical stability of the tissue due to progressive alteration of the structure of the corneal stroma. This in turn causes a change of the corneal geometry, which can result in significant loss of visual acuity up to cornea-based blindness. This applies similarly for keratoglobus, pellucid marginal degeneration (PMD), post-LASIK corneal ectasia, progressive myopia, and other eye diseases.

2. The Prior Art

The corneal cross-linking of the collagen fibrils of the cornea by the introduction of riboflavin into the corneal stroma combined with UV-A irradiation is considered to be prior art. The stability of the cornea is thus to be increased and progression of the illness is to be prevented. The geometry of the cornea can also be altered by the cross-linking and a refractive correction can thus be performed on the eye.

Thus, WO 2012/047307 A1 describes a device for irradiating the cornea for the cross-linking of the collagen fibrils of the tissue, after riboflavin has been introduced as an agent (photosensitizer) into the cornea. The disadvantage of such a system is that the system can perform incorrect irradiation of the eye in the event of eye movements.

EP 1561440 A1 and WO 2012/127330 A1 each describe a device for forming and solidifying the cornea by placing a molded body on the cornea, through which the irradiation of the cornea and also the fixation of the molded body or the irradiation unit on the cornea is performed. The background of this invention is the fact that the refractive power (diopter) of the eye is very strongly dependent on the radius of curvature of the front face (surface) of the cornea. By way of a new shaping of the corneal surface using a suitable molded body, it is to be possible, according to the hypothesis of the two documents, to alter the refractive power of the eye by this device in a defined manner. It will not be discussed here whether this hypothesis is correct. In any case, an essential disadvantage of these two systems is that the suctioning onto the cornea is performed just where the irradiation is also performed, namely flatly on the corneal surface by said molded body. Suctioning on the corneal surface, as described in the two documents of the prior art, can easily result in injury of the corneal surface in the sense of corneal erosion, which can cause substantial pain lasting days for the patients. The classical method for irradiating the cornea, as described, for example, in WO 2012/047307 A1 is itself linked to corneal erosion and substantial pain, however, there are also newer approaches for treating keratoconus, where corneal erosion is no longer necessary and where the treatment can therefore take place without pain (A. Daxer et al. Corneal Crosslinking and Visual Rehabilitation in Keratoconus in One Session Without Epithelial Debridement: New Technique. CORNEA 2010; 29: 1176-1179}. Especially for those applications in which the epithelium can fundamentally be maintained during the treatment, these two devices from EP 1561440 A1 and WO 2012/127330 A1 have a substantial disadvantage because of the suctioning onto the corneal surface to be irradiated.

SUMMARY OF THE INVENTION

It is therefore an object of the present invention to provide a device and a method for irradiating the cornea of the eye, which enable cross-linking of the collagen fibrils while overcoming the disadvantages of the prior art. Various embodiments of the device and various associated methods for treatment are presented. Each embodiment and the associated method are also to be understood as a starting point for further embodiments, in that one or more parts or elements of the presented embodiments can in turn be combined with one or more parts and elements of other embodiments, so that new embodiments result.

The object is achieved by a device, which comprises at least the following elements:
 a ring body, which has a bearing surface embodied concentrically about a longitudinal axis of the device for the purpose of fastening the device on the eye,
 an irradiation channel for irradiating the cornea, which is located within the ring body,
 a light source, which, in the operationally-ready state of the device for emitting light into the irradiation channel, is attached inside the ring body,
 wherein the bearing surface for fastening the device is arranged outside the irradiation channel.

Because the bearing surface is provided outside the irradiation channel (specifically outside viewed in the normal direction to the longitudinal axis of the device or the ring body), the device is only applied to the eye outside the irradiated area in the operating state, the irradiated area itself is not additionally loaded by bearing surfaces of the device. The device according to the invention thus does not have any fittings for fastening on the eye inside the irradiation channel, which, in the operationally-ready state of the device, when it is fastened on the eye, touch the eye.

In particular, the irradiation channel can be open on the side facing toward the eye—in the operating state of the device—(=on the side facing away from the light source).

The bearing surface or a diameter of the bearing surface or a diameter of the ring body or a diameter of the suction ring is dimensioned in this case so that the fastening on the eye preferably takes place outside the cornea, or outside the limbus or in the region of the conjunctiva.

The form of the irradiation channel can fundamentally be arbitrary, however, it is embodied at least sectionally along the longitudinal axis, preferably as an interior (cavity) of a hollow cylinder, and is delimited by the inner wall of the ring body. The diameter of the exit opening, measured perpendicularly to the longitudinal axis, cannot exceed in this case the internal diameter (smallest diameter) of the suctioning surface, which is preferably arranged concentrically about the longitudinal axis. In a preferred embodiment variant, the smallest distance of the delimitation of the exit opening (exit surface) from the longitudinal axis is not to exceed the smallest distance of the inner bearing edge or the smallest distance of the suctioning surface from the longitudinal axis. The diameter of the irradiation channel, measured perpendicularly to the longitudinal axis, is preferably to be at least sectionally between 0.5 mm and 20 mm and, in a particularly preferred embodiment, is to be between 8 mm and 18 mm, for example, approximately 15 mm. The diameter of the exit surface (exit surface, irradiation surface) from the irradiation channel, measured at the height of the end face of the ring body or the inner bearing edge along the longitudinal axis, is not to exceed 12 mm if possible and the diameter of the profile of the inner bearing edge or the internal diameter of the suctioning surface is not to exceed greater than 10 mm if possible, so that the device part for fastening on the eye lies outside the irradiated area in any case or delimits it to the outside, measured perpendicularly to the longitudinal axis. In a preferred embodiment, fittings in the irradiation channel can touch the eye or the cornea, but without participating in the fastening of the device on the eye (for example, suctioning).

A light source in the meaning of the present invention is to be considered any radiation source which can emit electromagnetic radiation in the range of ultraviolet radiation to infrared radiation, but in particular ultraviolet radiation. In the operationally-ready state, the light source will generally not protrude beyond the ring body in the longitudinal direction.

The irradiation channel, which is located inside the ring body, could be formed in a particularly simple manner by the inner wall of the ring body.

The device according to the invention is essentially embodied as a ring body, which is arranged essentially (more or less) concentrically about the longitudinal axis. In a particularly simple case, the ring body is implemented as a hollow cylinder without cover faces, i.e., as a cylindrical jacket. The longitudinal axis of the device then corresponds to the cylinder axis. A ring body in the meaning of the present invention is any body which has a closed jacket, however, wherein the jacket encloses a longitudinal axis. At least one cavity is inside the jacket, which is open in the longitudinal direction on one side, in particular on both sides.

The ring body can have a concentric suction ring, which is arranged at one end of the hollow cylinder, for example, and an attachment, which is connected (in particular mechanically rigidly) to the suction ring, and a receptacle for the functional components, for example, light source, power source or power supply, electronics (control electronics). The attachment can be embodied in one piece with the ring body, in particular by way of the other end region of the ring body, facing away from the suction ring. The suction ring can be arranged on the end face of the ring body which forms the bearing surface.

One embodiment of the invention provides that the light source has a fixed, in particular nondetachable mechanical connection to a control electronics system for controlling the light source and the control electronics system, in the operationally-ready state of the device, are also attached inside the interior of the device defined by the ring body. The advantage of this embodiment is that a compact embodiment of the device and also a desired profile of the irradiation can be achieved simultaneously.

In a further embodiment, the functional components light source, power source or power supply for operating the radiation source, and electronics system (control electronics system) have a fixed—in particular nondetachable—mechanical connection among one another, which also contributes to the compact embodiment of the device, in particular if the power source is also arranged inside the ring body.

The light source, power source, and control electronics system could be fixedly installed in the receptacle, for example, and permanently connected to the attachment or the ring body. The receptacle represents in this case a closed—at least laterally (perpendicularly to the longitudinal axis)—interior of the device. The functional components are then not replaceable. That is to say, a receptacle in the actual meaning is not provided, since the functional components have a fixed, nonvariable spatial relationship to the ring body.

The entire device is preferably embodied as sterile as a medical single-use product. The entire device, including the installed functional components, is therefore embodied so that it is sterilizable either by means of ethylene oxide or gamma radiation. The ring body having suction ring and all of the outer parts of the device can therefore be embodied as an injection molded part made of biocompatible material, for example, PMMA or another suitable plastic. The device can fundamentally be embodied from any arbitrary suitable material.

The suction ring has a connector, using which the suction surface can be connected to a suction pump, so that the ring body is fastened by the generated partial vacuum on the eye.

To achieve the most compact possible embodiment of the device, which is only partially a disposable product, it can be provided that light source, control electronics system, and power source are enclosed by a shared housing. The housing can then be inserted into the ring body and also removed again, so that ring body and housing can be disconnected because of the detachable connection and one of the two parts can be reused.

Accordingly, one variant of the invention is that the ring body has a receptacle for a housing, in which at least the light source, but preferably further functional components are attached—in particular (mechanically) detachably.

The receptacle can be an integral component of the ring body and can be embodied in one piece therewith, however, it could also be manufactured as a separate part and then permanently or detachably connected to the ring body.

To ensure a defined distance between light source and eye in the case of the embodiment with housing in the operationally-ready state of the device, it can be provided that the receptacle has a stop limit, so that a housing can be introduced only up to a depth, which is directly or indirectly defined by the stop limit, into the ring body. In order that the housing cannot fall out of the ring body—away from the stop limit—additional holding devices, such as catches or clamp devices, can be provided.

To prevent a transfer of bacteria from a possibly nonsterile housing to the ring body and thereafter to the eye, it can be provided that the device has a housing envelope, which has a stop-limited receptacle for the housing, wherein the housing envelope can itself be introduced into the receptacle for a housing in the ring body, preferably in a stop-limited manner. In this case, in the operationally-ready state, the housing envelope is to enclose the housing on the base and laterally completely and in a leak-tight manner and should best protrude on its upper side.

One embodiment of the invention provides that at least the light source is enclosed by a housing, which has a base, which faces toward the irradiation channel in the operationally-ready state and is at least partially transparent to the irradiation light, which is generated by the light source. The light source is thus completely shielded from bacteria, and only the housing, but not the light source, has to be sterilized if necessary.

In the case of a housing envelope, it can accordingly be provided that the housing envelope has a base, which is at least partially transparent to the irradiation light, which is generated by the light source.

Different settings for the light source can be performed using a control electronics system for the light source. In particular, a control electronics system can be provided for the light source, using which the irradiation power is settable so that it decreases during the irradiation of the cornea.

The device according to the invention can have a cooling device (for example, fan, cooling body, cooling liquid, etc.) for dissipating the waste heat generated by the light source. The remaining components of the device are thus subjected to less heat and can be produced from materials having lower temperature resistance.

The method according to the invention for irradiating the cornea of an eye using a device according to the invention provides that the device is fastened on the eye and the irradiation power is varied during the irradiation of the cornea. To reduce the heating of the device, which rises with increasing irradiation duration, it can be provided that the irradiation power decreases during the irradiation of the cornea.

BRIEF DESCRIPTION OF THE DRAWINGS

For further explanation of the invention, reference is made to the figures in the following part of the description, from which further advantageous embodiments, details, and refinements of the invention can be inferred. In the figures.

DETAILED DESCRIPTION OF THE PREFERRED EMBODIMENTS

Figure 1:
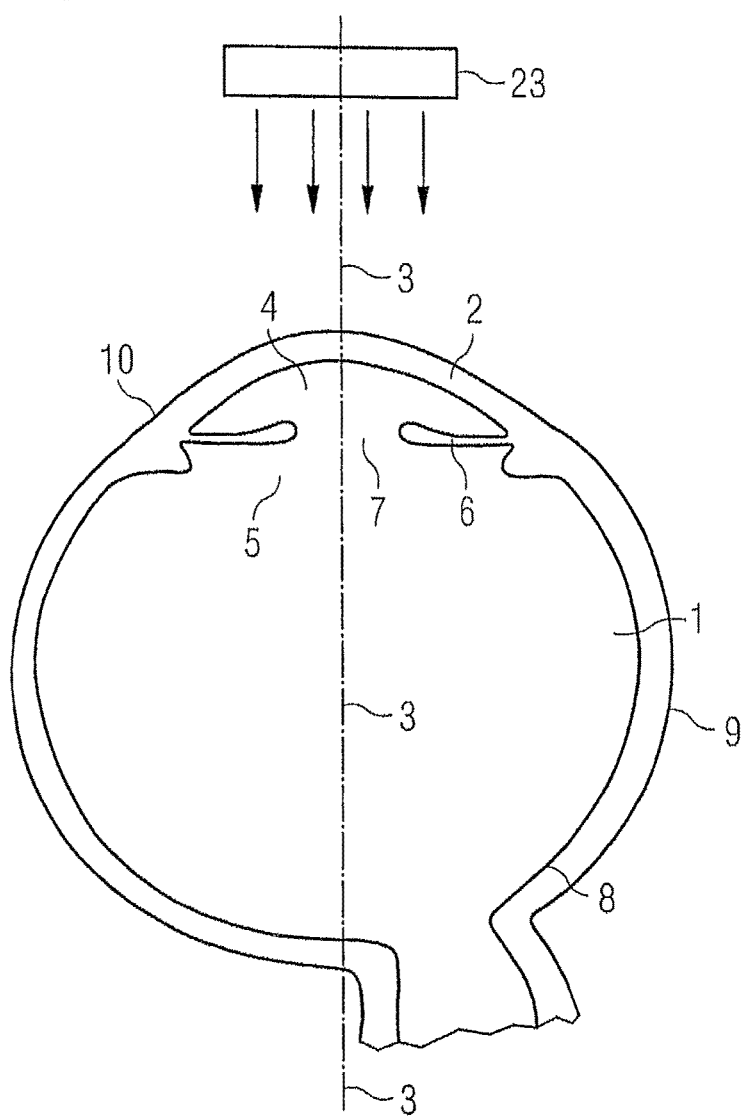
FIG. 1 shows a cross section through an eye with schematic light source.

The fundamental structure of the eye and the principle of the irradiation according to the invention are schematically illustrated in FIG. 1. The eye 1 is essentially a hollow sphere, which is delimited at the front by the cornea 2. The terms anterior and posterior are unambiguously defined in the anatomy of humans. The optical or anatomical axis of the eye, about which the eye 1 is functionally or anatomically arranged coarsely rotationally-symmetrically, is considered to be the axis of symmetry 3 of the eye. The anatomical axis and the optical axis are not necessarily coincident. Reference is made to the relevant technical literature with respect to the details on the relationship between optical and anatomical axes. The anterior 4 and the posterior 5 chambers of the eye are separated by the iris 6. The central opening of the iris forms the pupil 7, through which the light can reach the posterior chamber 5 of the eye and therefore the retina 8. Adjoining the cornea, the sclera 9 forms the outer wall of the eye 1. The sclera 9 is externally covered by the conjunctiva at least in the front part of the eye. The transition between cornea 2 and sclera 9 is referred to as the limbus 10. The cornea 2 has a front face (surface), which represents the external surface of the eye 1 to the front (the outside) and a rear face, which delimits the anterior chamber (anterior chamber of the eye) 4 to the front. The axis of symmetry of the eye 1 is to correspond as much as possible with the axis of symmetry or longitudinal axis 3 of the device. That is to say, the device is to be attached or aligned on the eye 1 as much as possible so that the longitudinal axis 3 of the device is aligned on the optical axis or anatomical axis of the eye 1 or an axis derived from these two axes of the eye. An axis of the eye derived from the optical or anatomical axis is considered, for example, an axis which extends through a point on the cornea surface, which extends on the linear or curved connection section between the passage point of the optical axis through the cornea (for example, first Purkinje reflex) and that of the anatomical axis (for example, pupil center point). In the case of the irradiation according to the invention, light from a light source 23 is preferably introduced in parallel to the axis of symmetry 3 of the eye 1 into the cornea 2. In a special embodiment, by way of collimators, which are introduced into the device (ring body or housing), an alignment of at least a part of the irradiation light can be achieved (irradiation direction), which does not necessarily have to be parallel to the longitudinal axis 3 and can enclose an angle different from zero (preferably between 0° and 90°) with the direction of the longitudinal axis.

Figure 2:
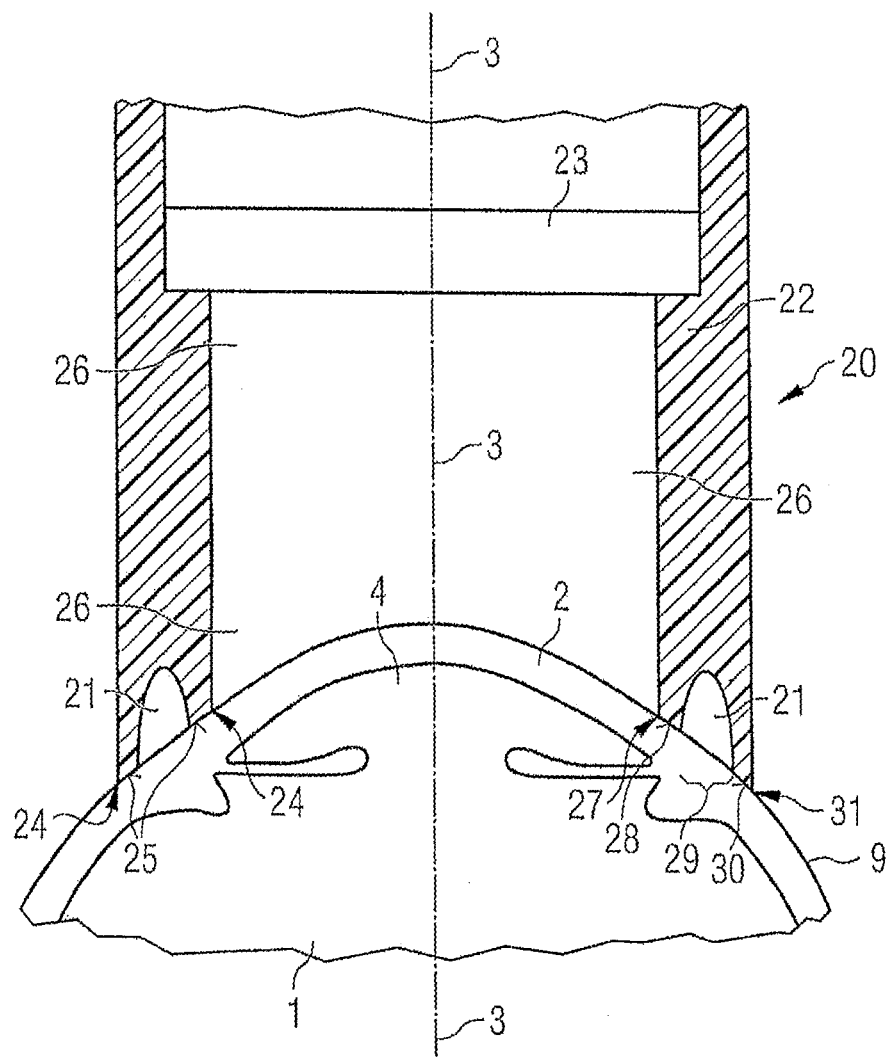
FIG. 2 shows a longitudinal section through a device according to the invention fastened on the eye.

A preferred embodiment of the device according to the invention is illustrated in FIG. 2. It has a ring body 20, which is implemented here essentially as a hollow cylindrical jacket. The ring body 20 has at one end a suction ring 21 for suctioning the device onto the eye 1 during the treatment. The suction ring 21 is implemented as a ring-shaped depression in the end face 25 of the ring body 20, an inner bearing surface 28 and an outer bearing surface 30 remain of the end face 25 inside and outside the suction ring 21. The area between inner and outer bearing surfaces 28, 30, which results by imaginary extension of inner and outer bearing surfaces 28, 30, forms the so-called suction surface 29. The end face 25 of the ring body 20, using which the ring body 20 bears on the eye 1 in the operating state, is delimited on the inside and outside by bearing edges 24, on the inside by an inner bearing edge 27 and on the outside by an outer bearing edge 31.

In this special embodiment, the ring body 20 has a receptacle 22 for a light source 23 for irradiating the cornea 2 or sclera 9. In this case, the suction ring 21 or the ring body 20 is embodied substantially concentrically about a longitudinal axis 3 of the device. Concentric means that the suction ring 21 or an equivalent structure, such as the bearing edge 24 or end face 25 (or the inner bearing edge 27, the outer bearing edge 31, the inner and outer bearing surfaces 28, 30), is arranged in a preferably closed, not necessarily rotationally-symmetrical geometry about the longitudinal axis 3 or a center point of the structure. Fundamentally, the suction ring 21 or the bearing edge 24 or end face 25 can have any arbitrary (closed) profile shape around a center, preferably the longitudinal axis 3. In this case, in a special embodiment, the longitudinal axis 3 does not have to extend linearly, but rather can also be curved or angled, or the like, along its profile. In a special embodiment, the bearing edge 24 is not closed along the circumference around the center or the longitudinal axis 3. In this case, it can be a segmented profile.

The suction ring 21 is separated on the inside, in the direction toward the longitudinal axis 3, by a bearing edge 27 or inner bearing surface 28, which is preferably formed concentrically to the longitudinal axis 3, and which is in contact with the eye 1 in the operationally-ready state or which touches the eye 1 or the conjunctiva or the peripheral cornea or the limbus 10, from an irradiation volume or an irradiation channel 26 or an irradiation opening or an irradiation region. The exit of the light from the device onto the cornea 2 therefore does not occur through the ring body 20 or the suction ring 21, but rather in the central area (recess of the device) along and about the longitudinal axis 3 of the device, which is adjoined on the outside, i.e., away from the longitudinal axis 3, indirectly or directly by the suction ring 21, which is not penetrated by the irradiation light. In other words, the suction ring 21 or the inner bearing edge 27 or the inner bearing surface 28 or the receptacle of the device encloses a central region of the device, which is arranged about the longitudinal axis 3, or delimits it to the outside, wherein the irradiation of the cornea 2 is performed in or through at least one longitudinal section of this central region, namely the irradiation channel 26. The irradiation opening (exit opening 19 for the light exit, see FIG. 3) or the irradiation area of the irradiation channel 26, on the one hand, and the suction ring 21 or the suction surface 29, on the other hand are not congruent and in a special embodiment are also not overlapping. More precisely, the irradiation area on the cornea 2, or the projection thereof on the cornea 2 in the direction of the longitudinal axis 3, and the suction surface 29 of the device on the eye 1 are not congruent or not overlapping.

In the present exemplary embodiment, the irradiation channel 26 is implemented cylindrically and concentrically about the longitudinal axis 3, the suction ring 21 is in the form of a circular ring, as are the bearing surfaces 28, 30, the bearing edges 24, 27, 31 are circular. In a special embodiment, the cornea 2 can protrude into the irradiation channel 26 in the operationally-ready state and the irradiation of the target tissue can be performed in the irradiation channel 26 or inside the ring body 20. In the proximal part of the ring body (for example, on the end face 25 of the ring body), therefore a molded body having suction function, through which the radiation light is radiated, is therefore at least not to be attached in any case. An actual exit opening thus does not exist during the treatment, but rather only i'n the technical sense, when the device is not fastened on the eye.

The inner bearing edge 27 or inner bearing surface 28 has a radius of at least 3 mm, preferably at least 4 mm and ideally between 5 mm and 6 mm, and in a specific embodiment 6 mm or more, about the longitudinal axis 3. The suction surface 29 of the suction ring is determined by the area (ring surface) between outer bearing surface 30 and inner bearing surface 28, wherein the radius of the outer bearing edge 31 (or bearing surface) is to be at least one-half of a millimeter, preferably greater than 1 mm and ideally greater than 2 mm or even 3 mm, larger than the radius of the inner bearing edge 27 measured from the longitudinal axis 3 of the device. Thus, for example, the inner bearing edge 27 (bearing surface) can have a diameter of 12.0 mm or 12.5 mm and the outer bearing edge 31 (bearing surface) can have a diameter of 18.0 mm or 18.5 mm.

In a special embodiment, there is only one of the two bearing edges 24 (bearing surfaces 28, 30), so that no special suction surface 29 is defined. In this case, the suction ring 21 is not embodied as a suction ring in the actual meaning. Independently thereof, the term suction ring also applies for this embodiment for the entire disclosure. In this case, the fastening on the eye is performed only by exerting a manual pressure on the device in the direction of the longitudinal axis toward the bearing edge.

In a further embodiment, shown in FIG. 2, the inner bearing edge 27 (inner bearing surface 28) is offset in relation to the outer bearing edge 31 (outer bearing surface 30) in the direction of the longitudinal axis 3, to be adapted better to the curvature of the eye or the cornea 2 or the sclera 9. This offset is, if possible, to be greater than 1 mm and less than 3 mm, for example, 1.5 mm, 2 mm, or 2.5 mm. In a special embodiment, the offset is at least 0.5 mm. The bearing surfaces 28, 30 do not have to be aligned perpendicularly to the longitudinal axis 3, but rather can additionally also enclose an angle with a plane perpendicular to the longitudinal axis 3 for still better adaptation to the curvature of the eye 1 or the cornea 2.

The receptacle 22 in FIG. 2 for the light source 23 can simply be implemented in the interior of the ring body 20 as a shoulder (stop limit, region having larger diameter than region of the ring body 20 located underneath (irradiation channel 26)): the inner, free diameter of the ring body is greater at the height of the light source 23 than in the irradiation channel 26. The light source 23 can then simply be placed on this receptacle 22, which is embodied as a shoulder, whereby the position of the light source 23 is fixed. This is also true similarly if a housing is present, which can be introduced into the receptacle of the ring body when the light source is located inside the housing and also if a housing envelope is present, into which the housing is inserted, and which is then inserted into the receptacle of the ring body. In these cases, the following applies: In the distal part of the housing (above the stop limit), the housing has an external diameter which is greater than the (every) proximal external diameter (below the stop limit). In the distal part of the housing envelope (above the stop limit), the (a) internal diameter is greater than the internal diameter of the proximal part (below the stop limit) of the housing envelope. This also applies to the external diameter of the housing envelope. The external diameter of the housing and the housing envelope is, at least sectionally along the longitudinal axis, preferably between 2 mm and 20 mm and, in a special embodiment, between 6 mm and 16 mm, wherein the wall thickness of the housing envelope (difference between external diameter and internal diameter) is preferably between 0.1 mm and 2 mm.

The mentioned diameters are measured perpendicularly to the longitudinal axis. The following convention is used for characterizing the direction along the longitudinal axis: In the anatomy of humans, the terms distal and proximal are used. Distal means away from the body and proximal means toward the body. Thus, for example, the hand is distal from the elbow joint and the shoulder is proximal from the forearm.

Since the present device is provided to be applied to the body of the human (to the eye), the device has a region which comes into contact with the body during the application of the device. This region of the device is the end, measured along the longitudinal axis, where the suction surface, the bearing surfaces, and the bearing edges are located and which is referred to in the description as lower or therefore, in analogy to the anatomy, without thus generating a reference to anatomical structures of the body, as proximal. Therefore, those structures of the device which, measured along the longitudinal axis, are relatively more remote from below (from the proximal region) are referred to as distal. Thus, for example, the receptacle for the light source is distal from the suction ring.

The functional components of the device (electronics 32, irradiation or light source 23, battery 33, etc.) are preferably arranged along the direction of the longitudinal axis 3, wherein they do not necessarily have to be attached along the longitudinal axis 3, but rather can also be located at a suitable distance from the longitudinal axis 3 inside the interior (receptacle) of the device, i.e., for example, inside the ring body 20 in FIG. 2.

Figure 3:
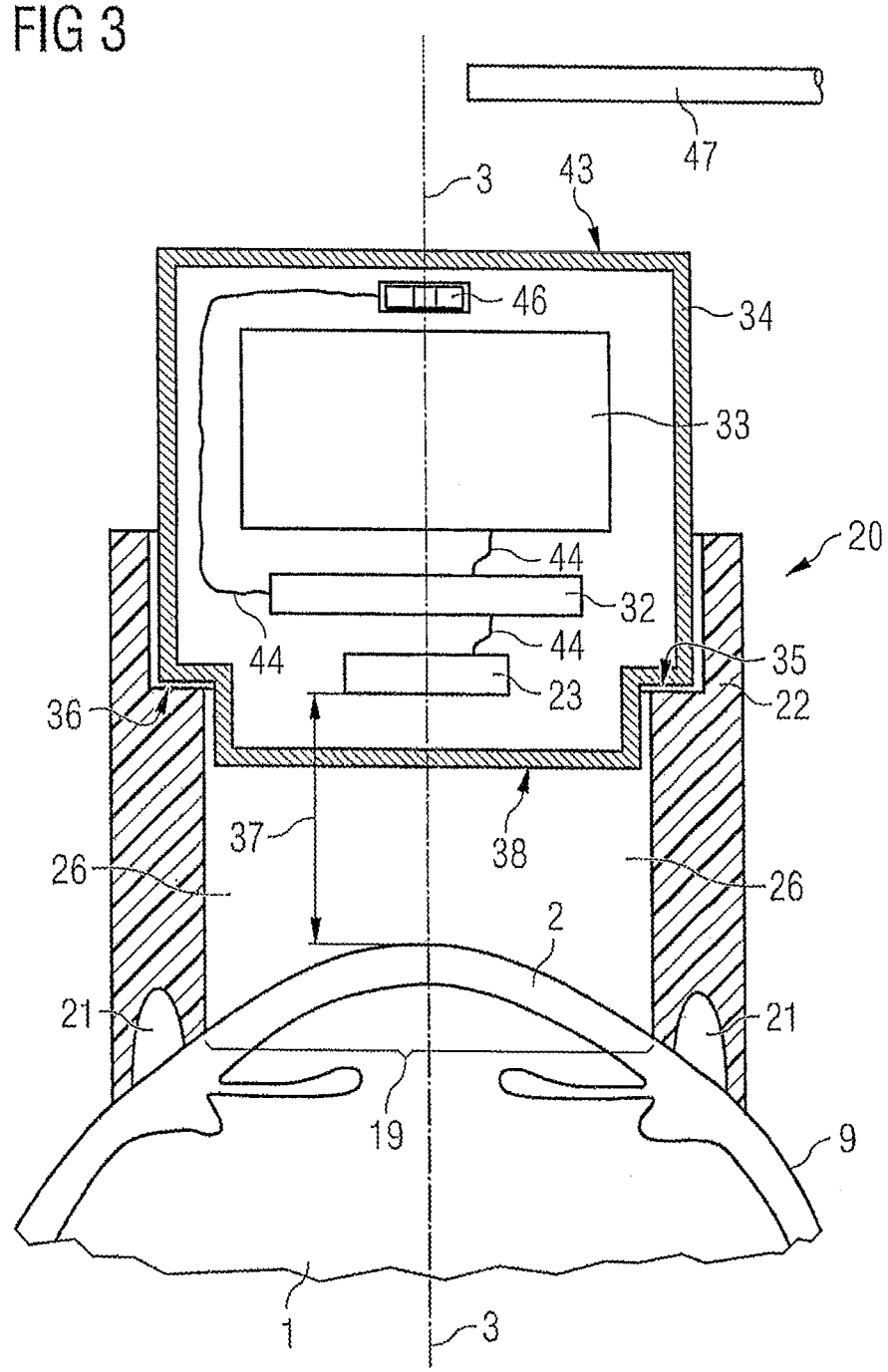
FIG. 3 shows the device from FIG. 2 with power source.

In a further embodiment according to FIG. 3, the ring body 20 is embodied in conjunction with the receptacle 22 such that the functional components (light source 23, control electronics system 32 for the light source, battery 33 as power source and a switch 46; all connected by electrical connections 44) are housed in a separate housing 34, which is not permanently connected to the ring body 20 and the attachment for the receptacle 22. The attachment for the receptacle 22 is implemented in this case in one piece with the ring body 20 and forms a part of the ring body 20. The receptacle 22 is thus embodied as a exchange receptacle, which enables the replacement of the functional components or the housing 34 from the device or from the attachment with the receptacle 22, which is connected to the ring body 20. In particular, the receptacle 22 is embodied such that the housing 34, which contains the functional components, can be introduced in a stop-limited manner into the receptacle 22 and also removed from the receptacle 22 again. The housing 34 also has a corresponding stop limit 35 which, in cooperation with the stop limit 36 of the receptacle 22, prevents an insertion of the housing 34 into the receptacle 22 beyond a defined depth. A defined distance 37 of the light source 23 from the corneal surface (or from the end face 25 of the ring body 20) and therefore a defined irradiation strength at the corneal surface is thus guaranteed. The distance of the light source 23 from the end face 25 of the ring body 20 or from the inner bearing edge measured in the longitudinal axis 3 is generally greater than 1 mm, preferably greater than 3 mm and, in a special embodiment, greater than 10 mm, but less than 70 mm, preferably less than 50 mm, and ideally less than 30 mm.

In the embodiment of the invention according to FIG. 3, the ring body 20 having attachment and receptacle 22 can be embodied from a resterilizable biocompatible material, for example, steel or titanium, and the housing 34, which contains the functional components, for example, can be embodied as a simple injection molded parts made of plastic, for example, made of PMMA, because the housing 34 is embodied, for example, as sterile (for example, ethylene oxide sterilization) as a single-use product.

The housing 34 can be embodied with or without base 38. The base 38 is used in this case as a window, which is either completely transmissive to the irradiation light or is differently transmissive in a spatially selective manner viewed over the irradiation area in dependence on the distance from the longitudinal axis 3 (radial) or the circumferential position of about the longitudinal axis (circular), i.e., depending on the location on the window surface measured perpendicularly to the longitudinal axis (i.e., at different locations at the passage points of the irradiation light through the window) and can therefore act as a beam profile converter (see below) in specific embodiments. The window 38 can also be embodied so that during the passage of the light through the window, the exit angle of the irradiation light from the window is different from the entry angle into the window, measured in relation to the longitudinal axis 3 of the device. The irradiation light is thus refracted during the passage through the window from or toward the perpendicular. The window can also be embodied so that the extent of this light refraction (angle change) is dependent on the position, i.e., the location on the window surface, i.e., on the distance from the longitudinal axis 3 or even on the position on the window surface, which extends perpendicularly to the longitudinal axis 3. The mentioned functions of the window can also be caused by suitable components which are attached above (distally) or below proximally) to the window, measured in the direction of the longitudinal axis, for example, by components in the form of inlay elements (for example, lamina) in the housing envelope.

In a special embodiment, a further or other window, which can also have the above-described properties, can be attached at another point inside or outside the housing 34 along the direction of the longitudinal axis 3, but in the irradiation direction after the light source 23. The window (the area or substance of the window) extends essentially perpendicularly to the longitudinal axis 3, although it can also have a differing or variable thickness along this extension. The thickness at each point of the extension (area) of the window is measured in the direction of the longitudinal axis 3.

Instead of the installed battery 33, an external current or voltage source can also be used. The battery 33 can also be provided externally, i.e., not in the device which can be placed on the eye, and connected using a cable or wire to the control electronics system 32.

Figure 4:
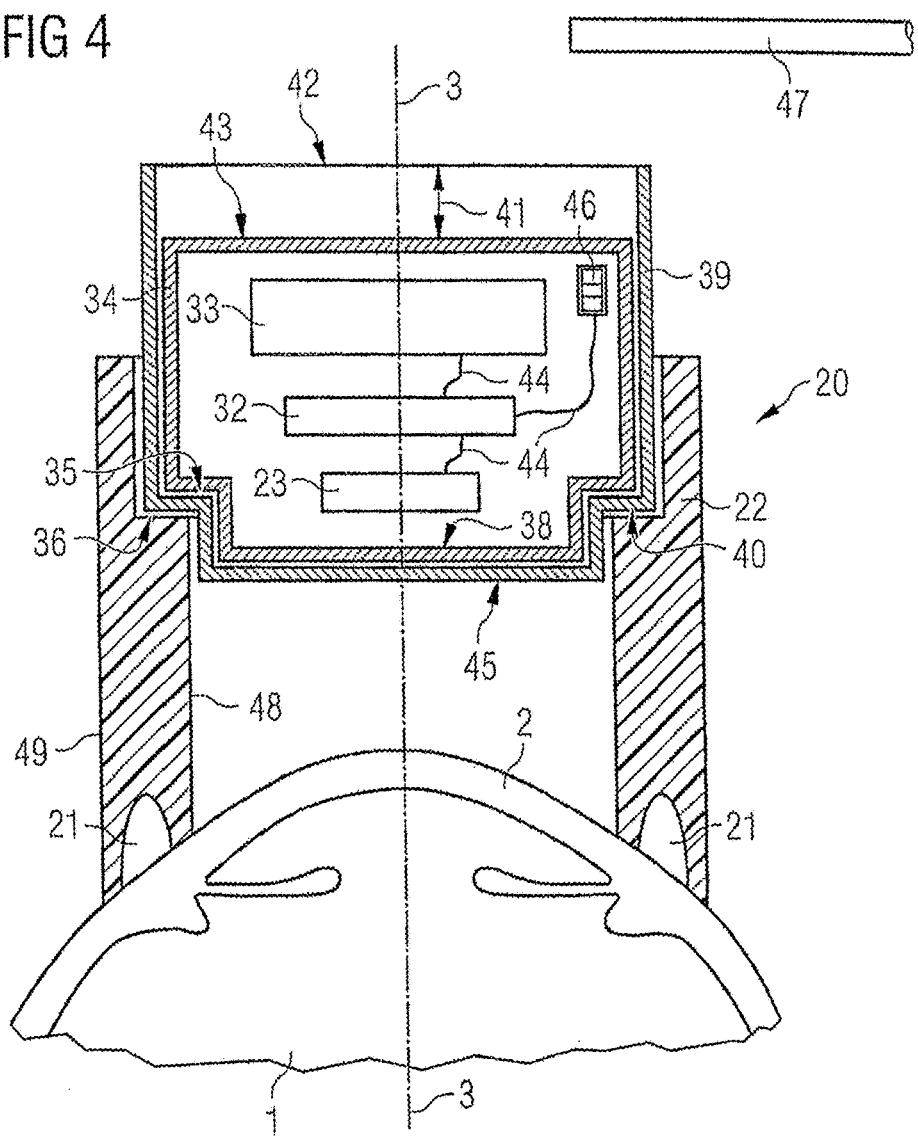
FIG. 4 shows an alternative embodiment of the device from FIG. 2 with housing and housing envelope.

In a further embodiment according to FIG. 4, in the operationally-ready state, in addition as an intermediate part between housing 34 for the functional components and the receptacle 22 (stop-limited exchange receptacle) of the attachment or ring body 20, a housing envelope 39 is attached, which itself in turn has an internal stop limit 40 for the stop-limited receptacle of the housing 34 and externally has a stop limit for the receptacle of the housing envelope 39, which receives the housing 34, in the receptacle 22 of the ring body 20. The housing 34, which contains the functional components (light source 23, control electronics system 32, battery 33, switch 36) thus does not have to be embodied as sterilizable, or does not have to be sterile. The housing envelope 39, which is to accommodate the housing 34, can therefore be embodied as a very simple and cost-effective injection-molded part made of biocompatible plastic (for example, PMMA) which is sterilizable using ethylene oxide or gamma radiation, as a single-use product. The external part of the device, i.e., the ring body 20 (having suction ring 21, attachment, and receptacle 22) can be manufactured as a reusable part, for example, for steam sterilization, for example, from steel or titanium or another suitable biocompatible material. In order that the sterility of the device can be ensured during the operation in this embodiment and a transfer of bacteria from the nonsterile housing 34 to the operating field is prevented, the height of the housing envelope 39, measured in the direction of the longitudinal axis 3, must be greater than that of the housing 34. The height of the housing envelope 39 in the operating state is preferably at least 1 mm greater than the height of the housing 34. The height of the housing is measured from the lower side 38 up to the upper edge 43 of the housing in the direction of the longitudinal axis 3. The height of the housing envelope is measured from the lower side 45 up to the upper edge 42 of the housing envelope in the direction of the longitudinal axis 3. This height difference 41 between housing 34 and housing envelope 39 is ideally greater than 2 mm, however, for example, 5 mm. In other words: the upper edge 42 (upper side) of the housing envelope 39 protrudes beyond the upper edge 43 (upper side) of the housing 34 in the perationally-ready state, i.e., when both are introduced in a stop—limited manner into the associated receptacles 22 of the ring body 20 or into the receptacle of the housing envelope 39, respectively, by more than 1 mm, preferably more than 2 mm, or ideally more than 5 mm. The upper edge is the point or edge or surface of the housing 34 or the housing envelope 39 which is the most distally remote from the body (eye 1, cornea 2) in the operationally-ready state. Thus, the point or edge or surface which is most remote from the suction ring 22, measured along the longitudinal axis 3. The suction ring 21 is proximal (below, rear). The receptacle 22 is distal (above, front).

In the operationally-ready embodiment according to FIG. 3, the ring body is preferably embodied as sterile (resterilizable) from metal or ceramic and the housing is embodied as sterile, preferably as a single-use product.

In the operationally-ready embodiment according to FIG. 4, the ring body is preferably embodied as sterile, the housing envelope as sterile, and the housing as nonsterile. Possible destruction of functional components can thus be avoided during the sterilization.

The device is preferably placed or attached in the operationally-ready state on the eye 1 so that the longitudinal axis 3 of the device is aligned essentially perpendicularly to the sagittal body plane, or approximately in the direction of the optical or anatomical axis of the eye 1. The longitudinal axis 3 of the device is preferably to correspond approximately to the extension direction of the optical axis or the anatomical axis of the eye, or is to continue it. The passage of the longitudinal axis 3 of the device through the passage opening (passage area) 19, which is enclosed by the suction ring 21, for the irradiation light (irradiation area, irradiation opening, . . . ) defines a center point (center), about which the suction ring 21 is concentrically arranged. This center point is, in the operationally-ready state, preferably to correspond approximately to the center point (center) of the cornea 2, which results from the passage point of the optical axis or the anatomical axis through the cornea 2. It is thus ensured that no damage to the limbal stem cells occurs, i.e., the limbus 21 is substantially excluded from the irradiation.

In various embodiments, the longitudinal axis 3 of the device can be aligned on different axes of the eye, i.e., continuing these axes of the eye. Thus, in one specific embodiment, the longitudinal axis 3 of the device can be aligned on the optical axis, or on the anatomical axis, or on an axis which lies between the optical axis and the anatomical axis.

The functional elements, e.g., light source 23, electronics system 32, battery 33, are also connected to one another by wire or cable (electrical connections 44) in this embodiment.

In one specific embodiment, the housing envelope 39 has an opening on the upper side (upper edge 42) for the insertion of the housing 34 into the housing envelope 39, preferably up to the stop limit 40. The housing envelope 39 or at least the window of the housing envelope is preferably embodied as transparent to the irradiation light.

In one specific embodiment, the properties of the lower side 45 (window) of the housing envelope (45) can entirely or partially correspond to those described above in FIG. 3 for the lower side (the base/the window 38) of the housing 34 and can act or be embodied at least partially as a beam profile converter.

In all embodiments having exchange receptacles, the replaceable elements of the device, such as housing 34 or housing envelope 39, are preferably inserted in the direction of the longitudinal axis 3 from above (distally), that is the end of the device (of the ring body 20) opposite or facing away from the cornea 2 or the suction ring 21.

The parts of the device which have a exchange receptacle (ring body 20 having receptacle 22, housing envelope 39) are embodied as open upward (distally), for example, on the upper edge 42.

In one specific embodiment, a switch 46 for turning on the light source 23 (for example, UV LED) is embodied as a mechanical switch. In another special embodiment, this switch 46 is embodied as contactless, for example, in that the housing 34, which contains the functional components, also has a magnetic sensor having switch or switch function, which is capable in the event of sufficient magnetic field of turning on the operating current for the light source or triggering the beginning of the irradiation and, in a further specific embodiment, also the end (the termination) of the radiation. In one specific embodiment, the irradiation time can also be defined or controlled via an internal, preferably electronic timer or clock, in that, for example, after turning on the irradiation by triggering a magnetic or other switch, after a specific preprogrammed time, the radiation is turned off automatically, i.e., without external action, by means of an internal timer (electronic timer inside the device (control electronics system 32)).

In one special embodiment, the turning on and/or off of the irradiation operation by the device is triggered by means of a sterile magnet 47 or magnetic rod, which is moved sufficiently close to the operationally-ready device by the operator or an operation assistant during the operation. In this case, the magnetic switch 46 is preferably located inside the housing 34. In this case, the magnet 47 or magnetic rod is part of the device.

Operationally ready is understood as the state of the device in which the respective parts of the device (depending on the embodiment ring body 20 (having suction ring 21), receptacle 22, housing 34, housing envelope 39, etc), are assembled and are in such a state (for example, temperature) that after the device is turned on (irradiation) it can be therapeutically used immediately in just this state.

The energy or radiant power transferred to the cornea 1 is the energy or radiant power which, depending on the embodiment, is preferably measured at a distance of 1 to 5 mm (for example, 3 mm) from the inner bearing edge 27 or from the end face 25 of the ring body 20 or between lower side of the housing envelope and 5 mm proximally to the lower side of the housing envelope (=between housing envelope and end face of the ring body), in each case on the longitudinal axis 3 and in each case inside the irradiation channel 26.

The irradiation channel is delimited proximally by the end face 25, distally by the light source 23, and laterally by the inner wall 48 of the ring body 20. In this case, the wall of the ring body 20 can be fenestrated, i.e., have openings.

For conventional irradiation by means of UV-A light with corneal cross-linking, a total energy of 5.4 J/cm$^2$ is to be transferred to the cornea 2. This total energy results from the multiplication of the power transferred to the cornea 2, which is normally between 3 mW/cm$^2$ and 30 mW/cm$^2$, by the irradiation time, which is accordingly between 180 seconds and 1800 seconds. In one specific embodiment, the timer is set (embodied) so that these conditions are met. In one special embodiment, the internal timer of the device is set (embodied) so that the device transfers an energy of less than 5.4 J/cm² to the cornea 2 during the irradiation. In one specific embodiment, the internal timer of the device is set (embodied), with preset irradiation power between 3 mW/cm² and 30 mW/cm² so that the energy transfer to the cornea 2 during the treatment time limited by the timer is less than 5.4 J/cm², in particular less than 5 J/cm², and very preferably less than 3 J/cm², preferably less than 2.5 J/cm² and ideally between 1.5 J/cm² or 1.8 J/cm² or 2.0 J/cm² and 2.5 J/cm², for example, approximately 1.8 J/cm², approximately 2.1 J/cm², approximately 2.2 J/cm², or approximately 2.3 J/cm². This means that the device or the timer (time switch) automatically turns off the irradiation after a time when the desired irradiation energy is reached according to the above considerations.

The internal timer (time switch) of the device therefore turns off the irradiation of the cornea 2, for example, according to following Table 1, depending on the embodiment, after the following irradiation time:

TABLE 1

| Power (mW/cm²) | Irradiation time(s) | Energy (J/cm²) | Irradiation time(s) | Energy (J/cm²) | Irradiation time(s) | Energy (J/cm²) |
|---|---|---|---|---|---|---|
| 3.00 | 720.00 | 2.16 | 780.00 | 2.34 | 600.00 | 1.80 |
| 6.00 | 360.00 | 2.16 | 390.00 | 2.34 | 300.00 | 1.80 |
| 9.00 | 240.00 | 2.16 | 260.00 | 2.34 | 200.00 | 1.80 |
| 12.00 | 180.00 | 2.16 | 195.00 | 2.34 | 150.00 | 1.80 |
| 15.00 | 144.00 | 2.16 | 156.00 | 2.34 | 120.00 | 1.80 |
| 18.00 | 120.00 | 2.16 | 130.00 | 2.34 | 100.00 | 1.80 |
| 21.00 | 102.86 | 2.16 | 111.43 | 2.34 | 85.71 | 1.80 |
| 24.00 | 90.00 | 2.16 | 97.50 | 2.34 | 75.00 | 1.80 |
| 27.00 | 80.00 | 2.16 | 86.67 | 2.34 | 66.67 | 1.80 |
| 30.00 | 72.00 | 2.16 | 78.00 | 2.34 | 60.00 | 1.80 |

The irradiation power in mW/cm² (or in mW upon observation of the total irradiated area) can be constant in this case during the irradiation time or can vary or oscillate around a specific value (or around a specific curve—see below). In a further embodiment, the irradiation power can follow a defined curve during the irradiation time, for example, linearly increasing or decreasing, nonlinearly increasing or decreasing, periodically varying, non-constantly linearly increasing or decreasing (i.e., during the irradiation time, the irradiation power increases or decreases linearly or nonlinearly in different strengths at different phases during this irradiation time), exponentially increasing or decreasing, etc., or an arbitrary combination of these curve forms.

Thus, for example, a non-constantly decreasing irradiation curve could follow the following law, for example:

$$\text{irradiation power}(t) = k1*t + k2*t + k3*t + f(t),$$

wherein k1, k2, k3, within the irradiation time or within a specific time phase during the irradiation time (wherein duration of the time phase is less than or equal to irradiation time) or in different time phases within the irradiation time, can be different constants or zero and f(t) can also be linear, multilinear, arbitrary, or zero within the irradiation time or in different time phases can in each case be differently linear, multilinear, arbitrary, or zero.

An embodiment variant in which the transferred total energy is approximately 5.4 J or 5.4 J/cm² and in which the irradiation power decreases with time, can appear as follows, for example (Table 2):

TABLE 2

| Zeit (s) | Leistung (mW/cm2) | Energie (mJ/cm2) |
|---|---|---|
| 15.00 | 17.80 | 277.50 |
| 30.00 | 16.70 | 536.25 |
| 45.00 | 16.30 | 783.75 |
| 60.00 | 15.80 | 1024.50 |
| 75.00 | 15.40 | 1258.50 |
| 90.00 | 14.80 | 1485.00 |
| 105.00 | 14.30 | 1703.25 |
| 120.00 | 13.80 | 1914.00 |
| 135.00 | 13.40 | 2118.00 |
| 150.00 | 13.00 | 2316.00 |
| 165.00 | 12.60 | 2508.00 |
| 180.00 | 12.30 | 2694.75 |
| 195.00 | 12.00 | 2877.00 |
| 210.00 | 11.70 | 3054.75 |
| 225.00 | 11.40 | 3228.00 |
| 240.00 | 11.20 | 3397.50 |
| 255.00 | 11.00 | 3564.00 |
| 270.00 | 10.85 | 3727.88 |
| 285.00 | 10.60 | 3888.75 |
| 300.00 | 10.40 | 4046.25 |
| 315.00 | 10.20 | 4200.75 |
| 330.00 | 10.10 | 4353.00 |
| 345.00 | 10.00 | 4503.75 |
| 360.00 | 9.91 | 4653.08 |
| 375.00 | 9.90 | 4801.65 |
| 390.00 | 9.85 | 4949.78 |
| 405.00 | 9.80 | 5097.15 |
| 420.00 | 9.75 | 5243.78 |
| 435.00 | 9.71 | 5389.73 |

Zeit = time
Leistung = power
Energie = energy

Figure 6:
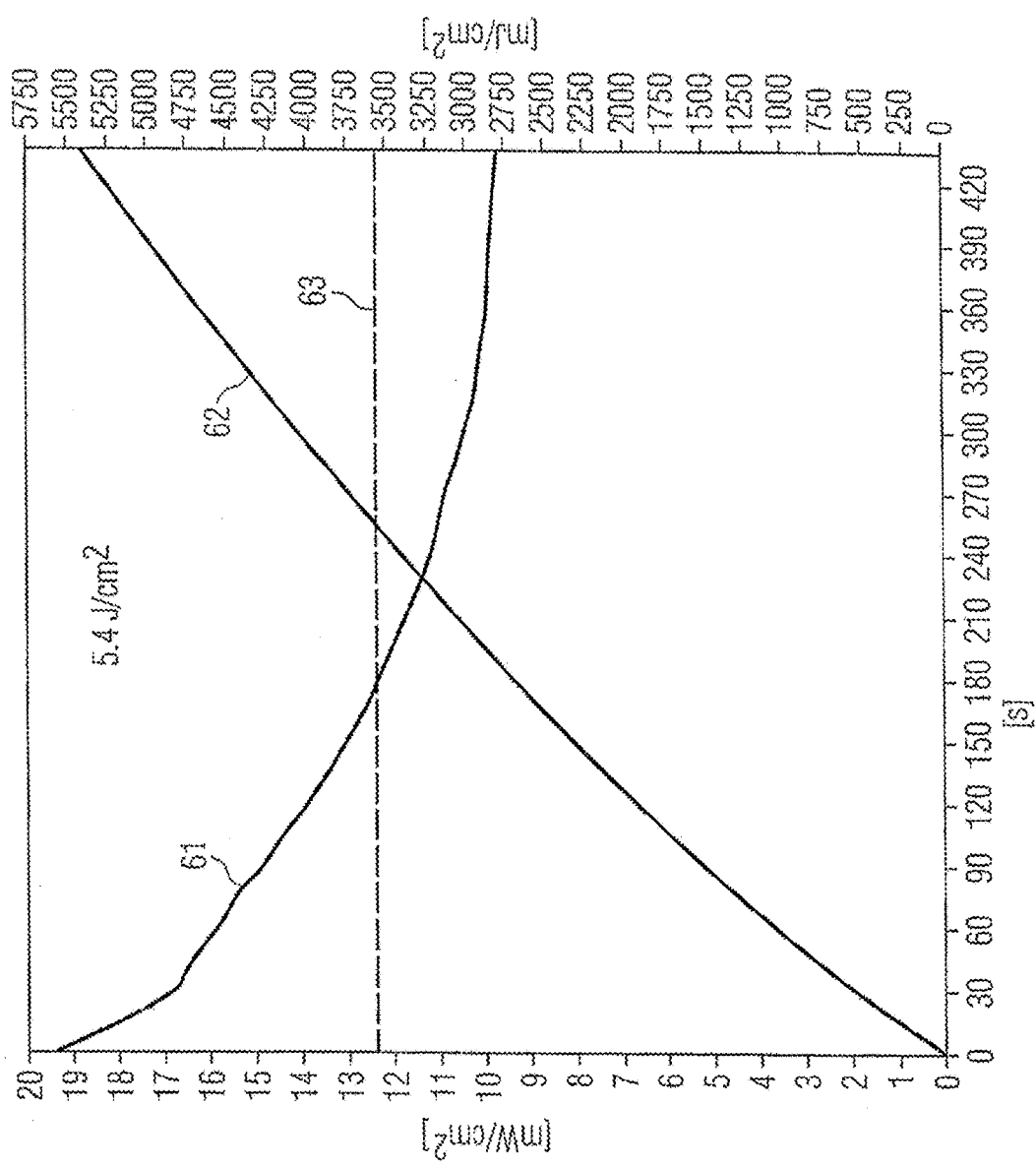
FIG. 6 shows a graph of the power introduced into the eye using the device according to the invention as a function of time.

This is shown in a graph in FIG. 6. The power in mW/cm² is indicated on the left vertical axis, the cumulative energy in mJ/cm² is indicated on the right vertical axis, and the time in seconds is indicated on the horizontal axis. In this case, the power (time curve 61 of the irradiation power) is shown decreasing, which transfers due to its special time curve a cumulative energy 62 to the cornea 2, which, at the end of the irradiation duration has thus transmitted the cumulative total energy of approximately 5.4 J (or 5.4 J/cm²) to the cornea 2. The mean irradiation power 63 results from the cumulative total energy divided by the irradiation duration.

Another embodiment variant, in which the total transferred energy is approximately 2.1 J or 2.1 J/cm² and in which the irradiation power decreases with time, can appear as follows, for example (Table 3):

TABLE 3

| Zeit (s) | Leistung (mW/cm2) | Energie (mJ/cm2) |
|---|---|---|
| 15.00 | 17.80 | 277.50 |
| 30.00 | 16.70 | 536.25 |
| 45.00 | 16.30 | 783.75 |
| 60.00 | 15.80 | 1024.50 |
| 75.00 | 15.40 | 1258.50 |
| 90.00 | 14.80 | 1485.00 |
| 105.00 | 14.30 | 1703.25 |
| 120.00 | 13.80 | 1914.00 |
| 135.00 | 13.40 | 2118.00 |

Figure 7:
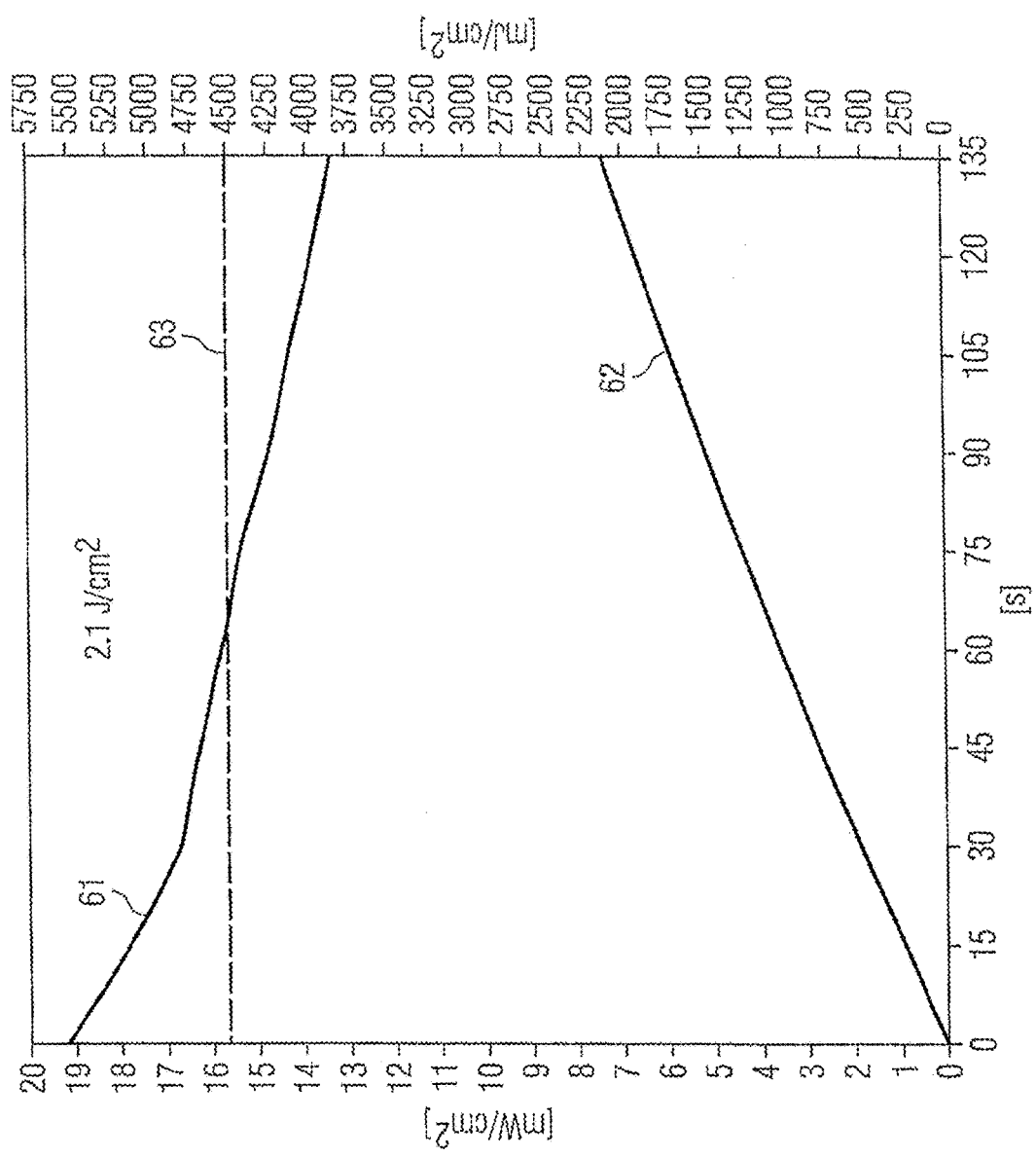
FIG. 7 shows a further graph of the power introduced into the eye using the device according to the invention as a function of time.

This is shown in a graph in FIG. 7, wherein FIG. 7 reflects the relationships of FIG. 6, but using a cumulative total energy of approximately 2.1 J (or 2.1 J/cm²) instead of 5.4 J (or 5.4 J/cm²). The variables plotted on the individual axes correspond to those in FIG. 6.

In one preferred embodiment, the irradiation power decreases during the irradiation time or at least at the beginning of the irradiation time with increasing duration.

That is to say, the irradiation power is less at a later point in time within the irradiation time than at an earlier point in time within the irradiation time. In a special variant of this embodiment, the decrease of the irradiation power decreases during the irradiation time. That is to say, in a later phase of the irradiation, the irradiation power decreases less strongly with time than in an earlier phase.

The transferred irradiation energy (total energy) is calculated from the integral of the time-dependent irradiation power over the irradiation time. The irradiation time is calculated from the duration which is required to reach the required total energy which is to be transferred to the cornea 2. This value is set (programmed) in a timer of the control electronics system 32 during the manufacturing.

This property, specifically that the power decreases during the irradiation, can be advantageous in that the technical requirements for the cooling or heat dissipation of the light source 23 in the operationally-ready state or during the operation are reduced and the costs of the manufacturing can thus be decreased. More advantageous materials can thus also be used in relation to the transparency of the housing (window) and the device can be constructed as particularly small, which is in turn accompanied by advantages in the medical application.

This is preferably a UV, in particular a UV-A light source 23 for irradiating the cornea 2 in this case. In a very special embodiment, the light source 23 is a light-emitting diode, which emits, for example, in the UV-A range, for example, light in a wavelength range between 350 nm and 370 nm (380 nm), for example, at 360 nm or at 365 nm or at 370 nm. A variation or inaccuracy of the functioning range of up to 10% around these values can be tolerated in specific embodiments. However, this light source 23 can also emit in a completely different wavelength range (visible or nonvisible) if an active agent for cross-linking or other influence of the collagen fibrils or another stabilizing element of the cornea 2 or this element itself are active in this wavelength range. Active in this context means that by way of the irradiation from the light source 23, with or without the aid of an agent (for example, riboflavin, hyaluronic acid, etc.) to be introduced into the cornea 2 or sclera 9 to mediate the effect, the cornea 2 is structurally or ultra-structurally changed such that a stabilization or shape change or refraction change or other change of the cornea 2 or sclera 9 is achieved.

A stabilization can be the inhibition or slowing of the progress of an illness or refraction anomaly or at least local hardening or shrinking of the tissue. The irradiation source (light source 23) can also consist of multiple individual irradiation sources (light sources) which can be arranged in any arbitrary position in relation to one another and which, in special applications, can also have different wavelengths or wavelength ranges in the emission characteristic. The irradiation sources or light sources can be attached at arbitrary locations inside the device, also outside the housing 34, preferably, however, all light sources are attached inside the housing 34.

The light source 23 or light sources can emit spatially or chronologically homogeneous or inhomogeneous electromagnetic waves for at least partial absorption in the cornea 2 or sclera 9. In a spatial aspect, the light source 23 can have a uniform intensity profile over the emission area or over the emission cross section, or a preferred directional characteristic, which can have intensity maxima in one or more different directions, for example. Thus, for example, a directional characteristic can be "club-like" having a specific opening angle (for example, 80°).

In another embodiment, the wavelength of the light source 23 is between 250 nm and 300 nm, in particular between 270 nm or 290 nm, or around or at 280 nm. The wavelength and the irradiation intensity of the cornea 2 are preferably selected so that no tissue ablation occurs on the cornea due to the irradiation. In one preferred embodiment, the wavelength and/or the irradiation intensity is selected so that a tissue ablation on the cornea is precluded.

In one special embodiment, however, the wavelength and the energy of the light source 23 (irradiation source) can be selected, however, so that a tissue ablation can be achieved on the cornea 2. In this exemplary embodiment, the wavelength is preferably to be between 180 nm and 230 nm. The energy is to be between 0.1 and 10 J/cm$^2$. The irradiated area on the cornea 2 is not to exceed a diameter of 12 mm, ideally it is to be 10 mm or smaller in diameter (for example, 9.5 mm, 9 mm, 8.5 mm, or 8 mm). The irradiated area is ideally approximately 1 cm$^2$ in size.

Figure 5:
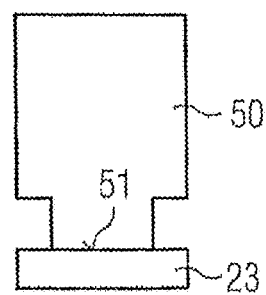
FIG. 5 shows a cooling body for a device according to the invention.

The irradiation or light source 23 (for example, LED) is, in a specific embodiment according to FIG. 5, directly or indirectly thermally connected to a solid, metallic, liquid, gaseous, ointment-like or pasty, greasy, creamy, amorphous, crystalline or other cooling body 50 or a mass inside the housing 34. The cooling body 50 or the mass is capable of absorbing at least a part of the heat generated by the light source 23. In other words: The temperature of this cooling body 50 increases on at least one point or area on its surface or in the body interior. This cooling body 50 is preferably at least 2 mm wide (measured in at least one dimension perpendicular to the longitudinal axis 3) and at least 2 mm tall (measured in the direction of the longitudinal axis 3). Ideally, this cooling body 50 is attached directly to the light source 23 by direct contact on a contact surface 51, wherein the distance between the cooling body 50 and a point on the external surface of the light source 23 is ideally zero if possible, but at least less than 2 mm, preferably less than 0.5 mm. The light source 23 can also be in contact with a liquid and/or a liquid can wash around it inside the housing 34. The irradiation light then penetrates this liquid. This liquid is capable of absorbing heat from the light source 23. The liquid thus heats up during the irradiation time.

In one special embodiment, the temperature of the device, in particular of the light source 23 and/or the ring body 20, in an operationally-ready state is less than 5° C., preferably less than 1° C., and ideally 0° C. if possible. In a further embodiment, the temperature of the device, in particular of the light source 23 and/or the ring body 20, displays a time-dependent curve during operation (=light emission from the light source). For example, the device is embodied so that the temperature of the device, measured at the light source 21 and/or the ring body 20, during operation (=for example, during the duration between turning on the irradiation operation and turning off the irradiation operation as induced by the internal timer) increases from a starting temperature (for example, 0° C.) in the operationally-ready state (starting state, before the turning on or before the point in time of the turning on of the device) to higher temperature values (for example, greater than 0° C., preferably greater than 1° C., and in particular greater than 5° C.).

However, the light source 23 can also emit in another UV range, in the visible light range, or in the infrared range.

Solid-state lasers (neodymium or titanium lasers—for example, Nd:YAG, Nd:glass, Nd:YLF, Ti:Sa) can also be used as the primary light sources. Corresponding harmonics of a basic wavelength can also be generated. Double-refractive crystals such as 880, KDP, KTP, or Li-niobate can be used for this purpose.

The current supply for operating the light source 23 can be produced locally via an "installed" (internal power source) battery 33 or an accumulator cell or, however, via a current line between light source and power source (battery, accumulator cell, power supply unit, or transformer) (external power source). "Installed" in this context means that the power source is permanently connected to the light source 23 such that it can be inserted jointly with the light source 23 into the insert of the suction ring (i.e., into the ring body 20), even if parts thereof protrude out of the ring body 20 or the receptacle 22. This connection can be performed, for example, by a shared housing 34, which not only electrically but also mechanically connects light source 23 and power source 33 such that the power source 33, due to the mechanical connection to the light source 23, automatically also has to be moved or is moved during the movement thereof (for example, insertion into the ring body 20). In other words, the power source 33 is seated fixedly or permanently connected by a mechanical device, at least during the intended use, on the light source 23. This can be implemented by a shared housing 34 or in the form of a shared base plate or other mechanical connecting elements between light source and energy source 23, 32.

By way of the attachment of the illumination unit (device) on the eye, which is achieved via the ring body 20 fastened on the eye 1, any uncertainty and incorrect illumination of the eye as a result of intentional and unintentional eye movements is prevented. WO 2011/138031 A1 does describe a tracking system for an illumination beam in the sense of a scanning spot beam to ensure a local irradiation distribution and to preclude errors due to eye movements, however, this system is very technically complex and costly. The possibility is accordingly provided by the fixation or possible fixation according to the invention of the device on the eye that the light source 23 (irradiation source) is itself also tracked with the eye movements and not only the beam from the light source 23 is deflected accordingly.

In a further embodiment of the present invention, a homogenizer can be installed to homogenize the active irradiation profile (intensity profile of the light source 23) in the irradiation channel 26 (between light source 23 and the end face 25 of the ring body 20) at least 1 mm proximally of the irradiation source (light source 23). This homogenizer is to produce a homogeneous intensity profile by "mixing" the primary beam profile between light generation inside the device and light exit from the homogenizer before the incidence on the corneal surface. Such a homogenizer can be embodied, for example, in the form of a reflective hollow cylinder, the cavity of which is aligned along the cylinder axis (longitudinal axis 3) or at a specific angle to the irradiation direction. (Such) a homogenizer can also be arranged concentrically or inclined or offset in parallel or a combination of these arrangements to the irradiation direction (which can be established, for example, by the longitudinal axis 3 between light source 23 and end face 25 of the ring body 20). The reflector surface of the homogenizer in the interior can be smooth or rough or uneven. It can have protrusions or projections, which reflect or do not reflect. The reflector surface can also have a spiral or circular—symmetrical or asymmetrical—surface design. A homogenizer can be implemented particularly simply if the irradiation channel 26 is formed by the inner wall 48 of the ring body 20 (see FIG. 4), because then the inner wall 48 can simply be implemented accordingly as a reflector surface.

In a further embodiment, the homogenized (homogenizer) or non-homogenized radiation profile (intensity profile) of the light source 23 can be converted into a radiation or intensity profile of specific characteristic by a suitable device, which is attached in the operationally-ready state between the light source 23 and the tissue to be irradiated (for example, cornea 2) or at a distance of at least 1 mm remote from the light source (proximally) or at least 1 mm remote from the end face 25 (distally) inside the irradiation channel 26. This device (beam profile converter) can be attached before or after the homogenizer if a homogenizer is present. If a homogenizer is not present, the beam profile converter is attached between light source 23 at a distance of at least 1 mm from the end face 25 and/or at least 1 mm from the radiation source inside the irradiation channel 26 (i.e., between light source and target tissue). The beam profile converter can be directly or indirectly mechanically connected to the ring body 20 or also, as already stated above, arranged in the housing 34, attached on the window (base 38, lower side) of the housing 34 or can replace this window or can be attached on the window (lower side 45) of the housing envelope 39 or can replace this window. In one specific embodiment, it can be permanently connected to the ring body 20 or can be replaceable or exchangeable—i.e., it can be inserted or removed. This can be used, for example, to compensate for the differing energy density of the light upon incidence on target tissue (cornea 2) is curved or inclined in relation to the irradiation direction in joules per unit area or Watts per unit area. Such a device for modification of the beam profile (beam profile converter) can consist, for example, of an insert or at least partial optical obstruction in the illumination beam path between the light source 23 and the target tissue (for example, at a distance of at least 1 mm from the end face 25 and/or at least 1 mm remotely from the light source inside the irradiation channel 26). This device (insert, housing, housing envelope, etc.) for beam modification is characterized in that it represents a transmission obstruction over at least a part of the irradiation area (intensity profile). In a special embodiment, this can be achieved by a lamina which is introduced into the beam path and consists of a material which displays an absorption behavior for the wavelength used. The intensity variation (beam modification) over the irradiation cross section (irradiation area) can be achieved in this case by thickness variation of the lamina over the illumination cross section. In this case, the thickness variation measured in the direction of the longitudinal axis of the lamina over the illumination cross-section measured perpendicularly to the longitudinal axis is a depiction of the desired intensity variation. The illumination cross section is considered the cross-sectional area within the irradiation channel proximally of the illumination source (i.e., between illumination source and end face or bearing edge) which extends perpendicularly to the longitudinal axis and is delimited by the inner wall of the ring body. In the case of a nonhomogeneous beam profile, before the incidence on the lamina, the thickness variation must be weighted in accordance with the non-homogeneity of the primary beam before the incidence on the lamina to generate the desired final intensity profile upon incidence on the target tissue. In the case of a homogeneous primary beam before incidence on the lamina, for example, to compensate for the effective drop of the light action on the peripheral tissue as a result of the cornea curvature, the lamina must have a thickness distribution in which the thickness preferably decreases symmetrically from the inside (approximately corresponding to the optical axis) to the outside (light beams incident on the peripheral cornea). The extent of the thickness or the thickness reduction is dependent on the absorption behavior of the lamina (for example, window in the base 38 or window in the lower side 45), i.e., the coefficient of absorption, and the precise or approximate curvature profile of the cornea 2 (depending on the required precision of the correction) toward the outside. However, the variation of the cornea thickness or any arbitrary other possible reason for a fundamentally arbitrary variation of the lamina thickness, or a combination of reasons, can be used for variation of the irradiation intensity.

Such a beam profile converter can also be used, with slight variation of the components for the primary light source 23 (tolerance of the components) with respect to beam characteristic of the primary light source 23 (photodiode, light-emitting diode, UV light source, LED, laser, laser diode, etc.) as a homogenizer.

To change or limit the beam diameter of the irradiation light, in the operationally-ready state, an aperture or an aperture system can be attached (for example, in the housing 34 or in the housing envelope 39 or on the ring body 20) inside the irradiation channel 26 or at the exit of the irradiation light from the irradiation channel 26. Such an aperture or such an aperture system consists of a material which is nontransparent to the wavelengths of the irradiation light having at least one or more transparent light passages applied thereon. These light passages can have an arbitrary shape, for example, they can be round, circular, elliptical, star-shaped, polygonal, or other. The apertures can be embodied as inlay lamina to be laid in the housing envelope 39. The light passages can have dimensions (for example, diameter or greatest extension) of 0.01 mm to 10 mm, measured perpendicularly to the longitudinal axis 3. The aperture can also be embodied as an "inverse aperture", in that at least one nontransparent area is at least partially enclosed by a transparent area.

In the case of all fittings (homogenizer, beam profile converter) in the interior of the ring body which protrude into the irradiation channel 26, it is to be ensured that they do not touch the cornea 2 in the operationally-ready state of the device. In this regard, these fittings—viewed from the light source 23 in the direction of the longitudinal axis 5—should be arranged in front of the end of the ring body 20, in particular at a distance of at least 1 mm remote from the inner bearing edge 27 (see FIG. 2).

The ring body 20 (or its linear outer wall 49, see FIG. 4) has, in the operationally-ready state, measured in the direction of the longitudinal axis 3, a height of at most 150 mm, ideally at most 70 mm and at least 10 mm. The light source 23 is at least 1 mm remote from the base 38 in the housing 34. The light source 23 is, in the operationally ready state, at least 1 mm, at most 150 mm, remote from the inner bearing edge 27 of the ring body 20. A typical height of the ring body 20 is approximately 30 mm and the entire device, including housing 34 and housing envelope 39, is approximately 60 mm.

The device according to the invention for irradiating the target tissue can also contain an electronics system (control electronics system 32) for current limiting for the current supply of the primary light source 23. This electronics system 32 can achieve this current limiting either by pulsation of the light source 23 with fixed or variable pulse duration for the power control of the primary light source or by limiting the current strength by ohmic or active components. The electrical activation of the light source 23 can be performed in a special embodiment via a constant current source, wherein the current through the irradiation source is to be at values around 100 mA (50 mA to 200 mA). The pulsation (pulse duration or relative pulse duration in relation to the period length) of the light or of the activation current of the light source can be arbitrary. A pulsation of approximately 1:2 for the ratio of pulse duration to period duration is advantageous. The pulsation can preferably be between 1:1 and 1:5. For example, at 1:1.5, 1:2, 1:3, 1:4, 1:5 or also greater than 1:5. The pulse duration can be in the range of seconds, ms, ns, ps, or less.

The standby current of the electronics system 32 is to be in the microampere range if possible, i.e., less than 100 IJA, preferably less than 10 IJA.

The irradiation intensity, power, and energy at the target tissue can be oriented, inter alia, according to the choice of the selected active agent in the target tissue, according to the desired irradiation duration, according to the desired two-dimensional action distribution (effect) along the surface of the target tissue (for example, cornea surface), according to the depth or depth distribution in the target tissue, according to the wavelength or the wavelength spectrum of the light source 23 (primary light source or upon incidence on the target tissue, or upon exit from the device), etc.

In one specific embodiment, the emitted power of the device on the target tissue, i.e., the power immediately after the light source 23 (for example, less than 1 mm remote from the light source) can be between 1 and 30 mW/cm$^2$, preferably between 3 and 20 mW/cm$^2$. In further embodiments, the emitted power can be between 3 and 15 mW/cm$^2$ or between 3 and 9 mW/cm$^2$. The power can be set (embodied) variably between the specified values or fixedly at a specific value in one of the specified ranges. Thus, in embodiments having fixed power setting, for example, 3, 6, 9, 10, 12, 15, 20, 25, or 30 mW. In one specific embodiment, the power can be greater than 30 mW/cm$^2$. In these cases, emitted powers of 30, 35, 40, 45, or 50 mW/cm$^2$ are thus conceivable.

In one embodiment, the current strength for activation or for operation of the primary light source 23 (for example, UV LED), can be limited to less than 700 mA In a further embodiment, this current strength can be limited to less than 200 mA In further embodiments, the device contains a voltage source for operating the primary light source 23 having a current limit to less than 200 mA, less than 150 mA, less than 125 mA, or less than 100 mA.

In one embodiment, the device for irradiating the target tissue contains a battery 33 having a voltage of 3 V to 9 V (or up to 12 V), preferably of 6 V, as a power source for the operation of the primary light source 23.

In one embodiment, the device for irradiating the target tissue contains a battery 33 having a capacitance less than 3700 mAh. In a further embodiment, the capacitance of the battery 33 is from 50 to 3700 mAh, preferably less than 1500 mAh. In a further embodiment, the capacitance of the battery is less than 200 mAh, or less than 150 mAh. In a special embodiment, the capacitance of the battery is around 100 mAh, for example, 90 mAh, 100 mAh, 105 mAh, i.e., approximately between 80 and 120 mAh. In this special embodiment, with suitable selection of the primary light source 23, the current for the operation of the primary light source 23 can be produced by the limiting of the capacitance of the power source, so that even in the event of malfunction, a provision of an excessive amount of power can be prevented as a safety measure, since the battery 33 itself cannot provide a sufficient amount of energy. In this case, the device for irradiating the target tissue must have a device for simple replacement of the battery 33, preferably on the upper side (on the side facing away from the target tissue or from the end face 25) of the device, or laterally. In a special embodiment, the battery 33 is permanently installed in the housing 34, so that it cannot be replaced by the user of the device.

In a further embodiment, a fuse is connected in the operating power circuit to the primary light source 23. This fuse is to have a response time for interrupting the power circuit of less than one second, ideally less than 0.1 second.

In a further embodiment, a timer for turning off the device (for example, turning off the operating current, blocking the illumination of the target tissue, etc.) between 1 and 30 minutes of operating time or irradiation time is planned. In a further embodiment, this timer can be preset to a specific point in time, for example, 15 minutes or 12 minutes or 10 minutes or 9 minutes or 6 minutes or 3 minutes.

In specific embodiments, the timer can be set during the manufacturing, for example, if the irradiation power during the irradiation is not constant, but rather, for example, has a decreasing curve, so that the chronological cumulative total energy during the treatment reaches the desired value (for example, 5.4 J or 5.4 J/cm$^2$), depending on the curve of the irradiation power.

The selection of the operating or irradiation time can be dependent, for example, on the selected power, wavelength, intra-corneal agent, tissue thickness, etc.

In one specific embodiment, the device can be equipped with an applanator for mechanically changing the cornea geometry by pressing the applanator onto the tissue surface (for example, corneal surface). This applanator can be embodied from material which is transparent to the selected wavelength of the light source 23 (for example, quartz glass) or material which is absorbent (for example, PMMA). The applanator can have an arbitrary surface geometry toward the tissue (i.e., toward the end face 25 of the ring body 20). The surface geometry can also be planar, convex, or concave. By way of the suitable selection of the surface geometry, in one embodiment, the inhomogeneous beam geometry (intensity distribution) or the influence of the cornea 2, which is curved peripherally in relation to the beam, can be compensated for, in that a convex applanator (for example, centrally protruding or convex) is used.

The applanator can also be connected to a device for beam modification. Thus, for example, the applanator can be embodied as planar orthogonally to the irradiation direction toward the target tissue (i.e., toward the end face 25 of the ring body 20) and as convex having an absorbent material for the selected irradiation wavelength facing away from the target tissue in the direction of the primary light source 23. The applanation surface or the applanator can be embodied from a material which is transparent or at least partially absorbent for the selected light wavelength in this case. If an applanator is used, it is intentionally accepted that the cornea 2 is touched by the applanator in the irradiated region, however, in this case the stress of the cornea 2 is less in comparison to fastening of the irradiation device in the irradiated region.

The suction ring 21 consists of two concentric bearing surfaces, for example, the inner bearing surface 28 and the outer bearing surface 30, or bearing edges on the target tissue, which are separated from one another by a partial cavity and which can accommodate or build up the partial vacuum for suctioning the device onto the target tissue.

The ring body 20 can be made of an arbitrary, preferably biocompatible material. It can be manufactured, for example, from plastic (for example, PMMA) or metal (steel, titanium, etc.). The ring body 20 can contain or consist of a magnetic material. The light source 23 can contain magnetic sensors (for example, Hall sensors), which detect the magnetic material upon insertion into the ring body 20 and can be used, for example, as the on switch for the light source 23. Other sensor systems are also conceivable.

The ring body 20, for example, the suction ring 21, or the housing envelope 39 can be equipped with a device, which enables wetting of the cornea 2 by means of water or aqueous solutions during the treatment. Thus, for example, the housing envelope 39 can have, up to a certain extent (for example, approximately 1 ml or less or also more, depending on the device) on the window side (on the base 45), one or more perforations, through which the water or the aqueous solution for wetting the cornea 2 slowly penetrates over the treatment time onto the cornea surface. The openings in the window (on the base 45) of the housing envelope 39 are to be smaller than 1 mm if possible in this case, preferably smaller than 0.5 mm.

Considered technically, in the operationally-ready state, every side wall of the housing envelope 39 and the housing 34, if it protrudes distally (above) over the actual ring body 20 (receptacle), represents an extension of the ring body 20 and can be counted with the ring body or considered equivalent thereto if needed.

All elements of all embodiments are combinable with one another to form further, novel embodiments.

LIST OF REFERENCE NUMERALS 1 eye
2 cornea
3 longitudinal axis (axis of symmetry) of the device, axis of symmetry of the eye
4 front chamber of the eye (anterior chamber)
5 rear chamber of the eye (posterior chamber)
6 iris
7 pupil
8 retina
9 sclera
10 limbus
11 —
12 —
13 —
14 —
15 —
16 —
17 —
18 —
19 exit opening (passage opening)
20 ring body
21 suction ring
22 receptacle
23 light source, irradiation source
24 bearing edge
25 end face
26 irradiation channel
27 inner bearing edge
28 inner bearing surface
29 suction surface
30 outer bearing surface
31 outer bearing edge
32 electronics system, control electronics system
33 battery (power source)
34 housing
35 stop limit on the housing 34
36 stop limit on the receptacle 22
37 distance between cornea 2 or corneal surface and the light source 23
38 base (lower side of the housing 34, window)
39 housing envelope
40 stop limit on the housing envelope 39

41 height difference between housing 34 and housing envelope 39
42 upper edge of the housing envelope
43 upper edge of the housing
44 electrical connection between the functional elements, for example, light source, electronics, and battery
45 lower side of the housing envelope
46 switch
47 magnet
48 inner wall of the ring body 20 or of the irradiation channel 26
49 outer wall of the ring body 20
50 cooling body (cooling device)
51 contact surface between cooling body 50 and light source 23
52 —
53 —
54 —
55 —
56 —
57 —
58 —
59 —
60 —
61 time curve of the irradiation power
62 time curve of the cumulative power transferred to the cornea
63 mean irradiation power, averaged over the irradiation time

What is claimed is:

1. A device for irradiating a cornea of an eye which comprises
    a light source which emits UV-A irradiation light in a wavelight range between 350 nm and 380 nm into an irradiation channel where said light source has an intensity profile with an opening angle and said irradiation channel is embodied as an interior cavity of a hollow cylinder and delimited laterally by a ring body, distally by the light source and proximally by the end face of the ring body and an irradiation opening, wherein the cornea can protrude through the irradiation opening into the irradiation channel, the irradiation allowing irradiation of a target tissue inside the irradiation channel or inside the ring body,
    a housing which encloses the light source, and
    a homogenizer installed in the irradiation channel to produce a homogeneous intensity profile on the cornea, wherein the homogenizer is arranged in the irradiation channel along a longitudinal axis as a reflector surface on an inner wall of the ring body.

2. The device according to claim 1, further comprising a power source comprising a battery having a voltage of 3 V to 12 V,
    wherein said battery is permanently installed in the housing.

3. The device according to claim 1, wherein the housing encloses the light source, a control electronic system and a power source.

4. The device according to claim 1, wherein the housing has a base which is used as a window to be completely transmissive to the irradiation light or differently transmissive in a spatially selective manner.

5. The device according to claim 1, wherein the housing contains a magnetic sensor having a switch function, and
    wherein the magnetic sensor is capable of turning on the light source or triggering irradiation when a sufficient magnetic field is present.

6. The device according to claim 1, wherein an internal timer turns off irradiation of the cornea when a defined total energy value of 5.4 J/cm$^2$ is transferred to the cornea.

7. The device according to claim 1, wherein emitted power of the device on the cornea is between 1 and 30 mW/cm$^2$.

8. The device according to claim 1, wherein emitted power of the device is greater than 30 mW/cm$^2$ but less than 50 mW/cm$^2$.

9. The device according to claim 1, wherein an internal timer is set to turn off irradiation of the cornea after an irradiation time between 60 seconds and 1800 seconds.

10. The device according to claim 1, wherein the reflector surface of the homogenizer at the inner wall of the ring body is rough or uneven to allow diffuse reflection of the UV-A irradiation light at the reflector surface.

11. The device according to claim 1, wherein the ring-body defines a distance between the light source and the eye ranging from 10 mm to 150 mm measured between the light source and an inner bearing edge of the ring body.

12. The device according to claim 1, wherein the ring-body is connected via a stop-delimited exchange receptacle to the housing.

13. The device according to claim 1, further comprising a receptacle defining a distance between the light source and the eye ranging from 10 mm to 150 mm measured between the light source and an inner bearing edge of the ring body.

* * * * *